United States Patent
Gaffar

(10) Patent No.: US 6,247,840 B1
(45) Date of Patent: Jun. 19, 2001

(54) DIALYSIS CONTAINER WITH SAMPLE SAVER

(75) Inventor: Shaik Abdul Gaffar, Northridge, CA (US)

(73) Assignee: Shaik A. Gaffar, Northridge, CA (US)

( * ) Notice: Subject to any disclaimer, the term of this patent is extended or adjusted under 35 U.S.C. 154(b) by 0 days.

(21) Appl. No.: 09/007,462

(22) Filed: Jan. 15, 1998

(51) Int. Cl.[7] .................................................. B01F 13/08
(52) U.S. Cl. ...................... 366/274; 366/273; 366/241; 220/212.5; 210/321.6; 210/321.63
(58) Field of Search ................................ 366/241, 273, 366/274, 127; 210/222, 223, 695, 321.74, 321.6, 321.63; 220/212.5

(56) References Cited

U.S. PATENT DOCUMENTS

| | | | |
|---|---|---|---|
| 4,192,748 | * | 3/1980 | Hyden ............................. 210/321.74 |
| 5,141,327 | * | 8/1992 | Shiobara ............................. 366/274 |
| 5,733,442 | * | 3/1998 | Shukla ............................. 210/223 |

* cited by examiner

Primary Examiner—David A. Reifsnyder

(57) ABSTRACT

A Revolutionary Dialysis Container for safe dialysis of biological samples is described. A handle with wide top gives a non-slippery grip to lift and carry the container by a human hand. On its bottom, the buffer reservoir possesses a Sample Saver, which is nothing but a flat top plate attached to a vertical side wall. The reservoir holds dialysis buffer and bags containing biological samples. The Sample Saver encloses a bar magnet. The flat top plate and the vertical side wall of Sample Saver have several openings for the free flow of buffer during dialysis. However, these openings eliminate physical contact between dialysis bags and the highly spinning bar magnet. Also, the flat top plate, because of special distribution of openings, suppresses the formation of vortex in buffer during mixing. This preassembled unit also provides safety to long dialysis bags. One can dialyze fast and save time. It is simple to use and practically free of maintenance.

22 Claims, 6 Drawing Sheets

DIALYSIS CONTAINER WITH SAMPLE SAVER

CROSS-REFERENCE TO RELATED APPLICATIONS

Not applicable

STATEMENT REAGARDING FEDERALLY FUNDED RESEARCH OR DEVELOPMENT

Not applicable

REFERENCE TO MICROFICHE APPENDIX

Not applicable

BACKGROUND OF THE INVENTION

The Revolutionary Dialysis Container specifically relates to dialysis of biological samples in biochemical and immunochemical studies.

In biochemical processes such as extraction, purification, conjugation and characterization, excess reagents are removed from desired molecules by dialysis. To perform dialysis a sample is taken in a bag with semipermeable membrane and stirred against buffer present in a large container. With time large molecules are retained inside the bag while small reagent molecules go out into buffer surrounding the bag. During dialysis, buffer is changed several times so that undesired molecules along with buffer are removed. Routinely, glass or plastic beakers are used to hold buffer. The first problem with these oversized containers is lack of proper grip. A slip causes loss of valuable sample, spill of reagents and breakage of the container. The second problem is in mixing buffer. Theoretically, fast mixing results in quick exchange of chemicals across the membrane. But, in practice, when buffer is mixed, a vortex develops and makes dialysis bag dive to bottom where either the bag pushes magnet go out of spin or magnet damages the membrane of bag. Also, some samples due to the presence of high amount of salt automatically sink to bottom and face similar consequences. These events not only impair dialysis but also result in total or partial loss of valuable sample. The third problem is in exchange of used buffer with fresh. Ordinarily, used buffer is poured out from the wide mouth of beaker. Dialysis bag and spin magnet often slip into sink and get contaminated with undesirable chemicals and materials. In other instances when samples contain radioactivity, therapeutic drugs or toxins, it is undesirable to touch or contaminate other surfaces. Therefore, there is a need for a better dialysis container.

Shibora in U.S. Pat. No. 5,141,327 describes a stirrer that includes a stator and a housing containing a rotor. The rotor is a hollow cylinder with openings at both ends and with slots in the center. The liquid which flows in through two communication ports of housing is sucked into the rotating rotor, mixed and returned through slots of rotor to the container through an additional port present in the center at the top of housing. This configuration has no mechanism to prevent dialysis bags of different diameters and lengths either blocking the ports or getting sucked into housing and then, into the rotating cylindrical rotor. Therefore, the dialysis bags may block the flow of liquid, may get ruptured by the rotor or may stop the motion of rotor itself. The unit is bulky and needs maintenance.

Hyden in U.S. Pat. No. 4,192,748 describes a dialysis apparatus where a long dialysis membrane forms a partition between a sample to be dialyzed and the buffer to be used in dialysis. This apparatus which has several peripheral equipment, is expensive, bulky, and requires extensive maintenance. It is highly suitable for patient care. For instance, blood is continuously pumped into apparatus to remove unwanted chemicals and the dialyzed blood is then returned to the body of patient.

Shukla in U.S. Pat. No. 5,733,442 describes a microdialysis system for the dialysis of microliter volume of biological materials. However, this system is not convenient for samples of higher volumes (several milliliters to deciliters). Placing a small magnet inside the chamber is cumbersome and inefficient for rapid stirring. Also, the magnet does not stir outside buffer surrounding the dialysis system. Besides, the area of membrane, and therefore the volume of sample, exposed for dialysis is small when compared to the area of an entire bag exposed to buffer. Hence, the microdialysis system takes a lot longer time to complete dialysis of samples.

OBJECTS AND ADVANTAGES

The objects and advantages of the Revolutionary Dialysis Container are:

(a) to provide in the buffer reservoir, a flat top plate and a vertical side wall (together called as Sample Saver) which irrespective of the speed of mixing prevent physical contact between delicate dialysis bag and highly spinning bar magnet;

(b) to provide apertures in the flat top plate and in the vertical side wall so that only buffer circulates but dialysis bag do not percolate;

(c) to distribute holes in the flat top plate away from its center so that formation of vortex in buffer is suppressed, and (d) to provide a handle, which has a wide top and which is separated from buffer reservoir by a large gap, so that a human can carry the unit with a non-slippery grip.

Further objects and advantages will be apparent from the following description and drawings.

BRIEF SUMMARY OF THE INVENTION

The Revolutionary Dialysis Container, with a built in handle and Sample Saver, is useful for safe dialysis of research biological materials. The side handle can be used by a research worker to lift and carry the unit and its contents with a firm grip. Sample Saver, a special device with a flat top plate and a vertical side wall, which is located inside the dialysis container, prevents physical contact between highly spinning bar magnet and delicate dialysis bag. However, it allows rapid mixing of buffer at all speeds of the enclosed bar magnet. Sample Saver, because of special spacial arrangement of apertures in its flat top plate, suppresses vortex formation in the buffer of container. Long dialysis bags safely rest on the flat top plate of Sample Saver.

BRIEF DESCRIPTION OF THE DRAWINGS

In the drawings, all closely related figures have the same number but different alphabetic suffixes.

REFERENCE NUMERALS IN DRAWINGS

Figure 1:
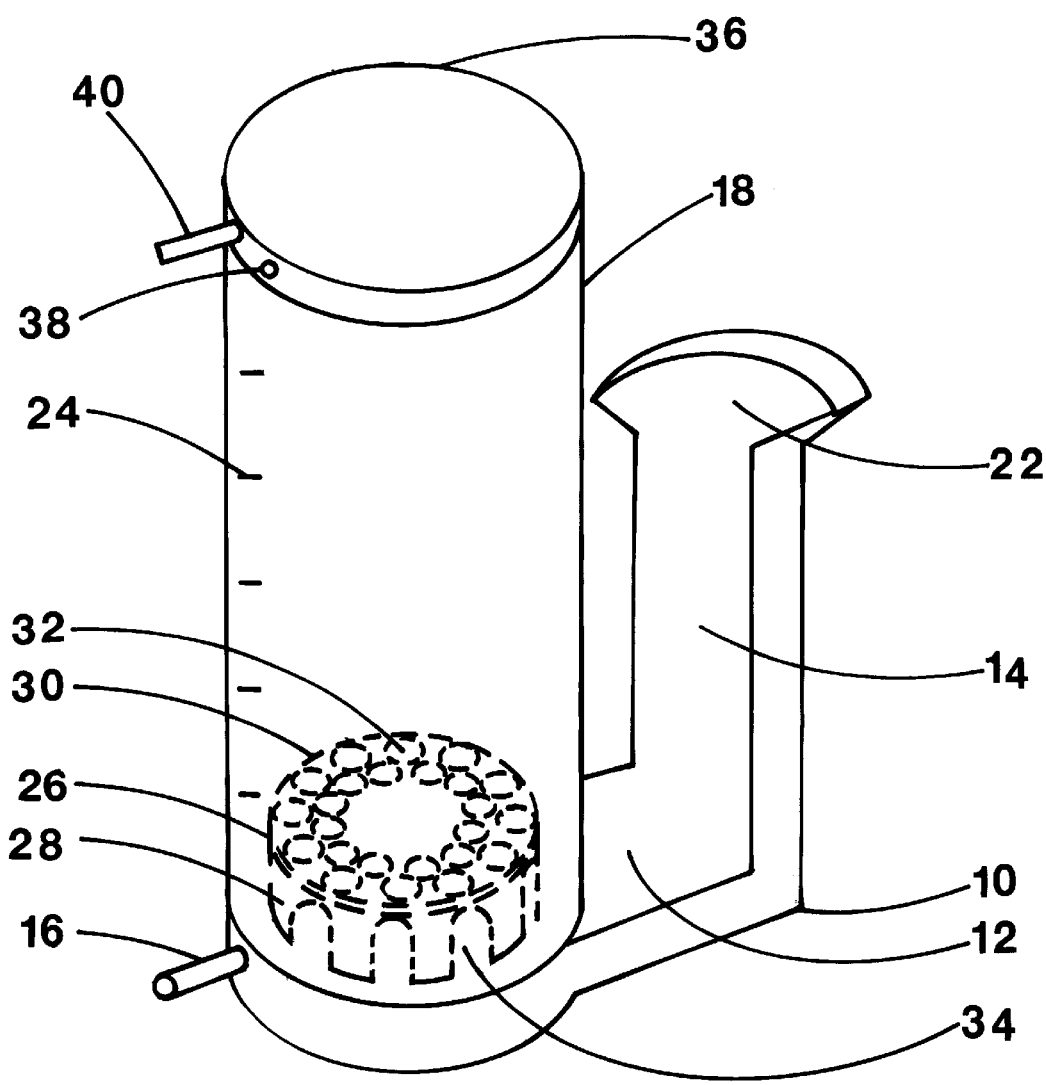
FIG. 1 shows a perspective view of the Revolutionary Dialysis Container.

10 L shaped plate
12 base plate
14 vertical handle
16 drain tube
18 reservoir
20 hole in base plate
22 handle top
24 graduation mark
26 Sample Saver
28 side wall
30 top plate
32 hole in top plate
34 groove
36 lid
38 hole in lid
40 stop pin
42 hole in the bottom of lid
44 groove in lid
46 Sample Bag Retainer
48 hole of Sample Bag Retainer
50 transverse slit of Sample Bag Retainer

DETAILED DESCRIPTION OF THE INVENTION

A perspective view of the first preferred embodiment of the Revolutionary Dialysis Container, is shown in FIG. 1. This unit has an L shaped plate 10 of uniform thickness. A single continuous piece of acrylic having length between 10" and 15", width between 4" and 7" and thickness between 0.3" and 1" is cut, shaped by machining and then bent in the middle of its length by applying heat. This results in a flat horizontal base plate 12 and a vertical handle plate 14 without any need for nuts and bolts. Slightly thick or thin, clear or colored acrylic can also be used for this purpose.

Most of the base plate is made broad to accommodate buffer reservoir. It carries a drain tube, made of brass, 16 in its rim and a reservoir 18 on its top. To fit drain tube, a hole of about 1" long is drilled in the middle of the rim perpendicular to the surface of the base plate. A suitably long piece of tube is then inserted and fixed permanently, using epoxy based glue. The drain tube is made to communicate with another short vertical hole 20 drilled in the top of base plate so that drain tube opens into the reservoir chamber FIG. 2.

Figure 2:
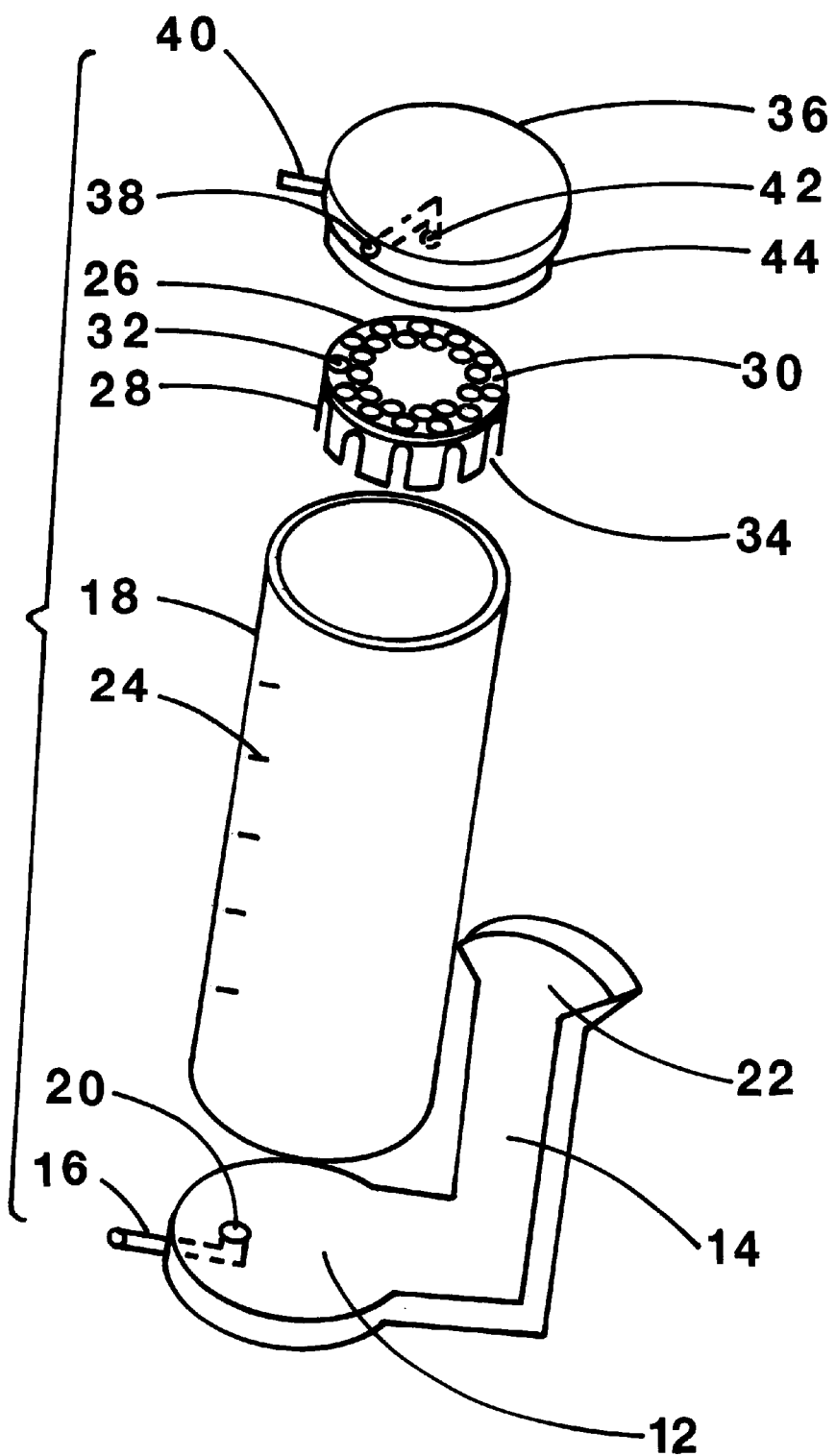
FIG. 2 shows an exploded view of the unit.

The vertical plate, which from its top to bottom has at least 1" gap from reservoir, forms a sturdy handle as shown in FIGS. 1, 2. The handle top 22 is made wide for a non-slippery grip.

The buffer reservoir, a clear transparent tube, has length between 6" and 10", outer diameter between 4" and 6" and wall thickness between 0.2" and 0.4" FIGS. 1, 2. One end of the reservoir is permanently attached to the top surface of base plate using solvent adhesive. The outer surface of reservoir is etched with graduation marks 24 to indicate approximate volume.

Figure 6:
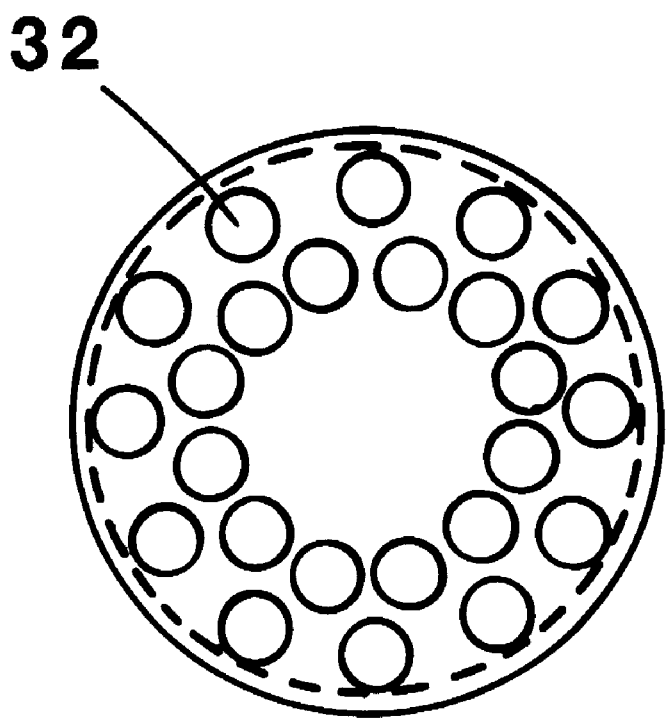
FIG. 6 shows arrangement of holes in the top plate of Sample Saver.

Sample Saver 26 fits in the chamber of buffer reservoir FIGS. 1, 2. It appears like an inverted cup having an outer diameter, between 3" and 5". The height of side wall 28 of the Sample Saver is between 1" and 3". The flat top plate 30 of the Sample Saver has holes 32. This top plate, which is attached in circumferential manner to the upper end of side wall, has holes as shown in FIG. 6. Several grooves 34 are cut across the side wall including the rim. With the remaining free edge of the side wall, Sample Saver is attached to the top of base plate by using solvent adhesive. The Sample Saver encloses a magnet with enough room to spin freely.

Figures 5A, 5B:
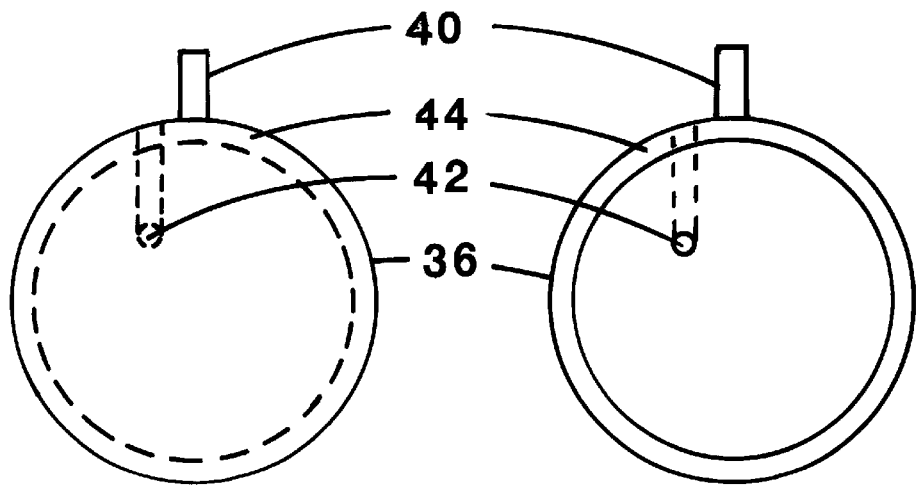
FIG. 5A shows lid of reservoir.
FIG. 5B shows groove in the lid of reservoir.

A lid 36 having outer diameter between 4" and 6", and thickness between 0.4" and 1" sits on the top of buffer reservoir FIG. 1. The lid has a hole 38 and a stop pin 40, made of brass, in its rim FIGS. 1, 2. The hole, which runs perpendicular to the flat surface of the lid, is approximately 1" long and is connected to another short vertical hole 42 made in the bottom surface FIG. 2. Together these holes open into the buffer chamber to provide ventilation. The lid in its flat bottom has a groove 44 along its rim FIGS. 5A, 5B. The groove accommodates the rim of reservoir. The stop pin is attached permanently to lid first by drilling a suitable hole and then by using epoxy based adhesive to hold the pin in place.

OPERATION

For operation, the user does the following in sequence:
(a) attaches a suitably long flexible plastic tube to drain tube 16 of base plate on one end and to stop pin 40 in the lid on the other end;
(b) adds required volume of buffer to reservoir 18;
(c) puts bag containing sample in the reservoir buffer;
(d) closes reservoir with lid 36; and
(e) places the entire unit on a magnetic stirrer and mixes the buffer.

After some time, to change buffer, the user disconnects the plastic tube from lid and places it in a sink to drain liquid. Then, reconnects the tube to lid before adding fresh buffer and continues mixing. At the end of dialysis, the user collects the sample bag before draining the buffer from container. Finally, the user rinses, air dries and stores the unit for next use.

The advantage of enclosing spin magnet in the Sample Saver which is attached permanently is that, unit is always ready for immediate use. Therefore, one can save time that is generally spent looking for a misplaced or a suitable spin magnet. The disadvantage is that spin magnet is not available for other uses. Locating stop pin in the lid helps specifically in controlling the hydrostatic pressure of liquid in the reservoir. Transparent wall of reservoir allows one to see the spinning of magnet located in the Sample Saver and the fullness of sample bag present in the buffer during dialysis.

DESCRIPTION OF OTHER EMBODIMENTS

The second preferred embodiment of the Revolutionary Dialysis Container contains a Sample Saver but the unit has no side handle, no drain tube, and the lid has no stop pin. The disadvantage is that used buffer can not be drained easily. However, by partially removing lid from the top of reservoir, a narrow slit can be opened through which used buffer can be drained. During draining, sample bag can be retained safely in the reservoir by controlling the width of slit with lid. The unit has to be transported by holding the buffer reservoir. Eventhough this type of container can be used for dialysis of a large number of biological samples, it is not appropriate for samples containing toxic substances.

When liquid in a container is mixed rapidly by a movable member such as a spin magnet, a vortex develops in the liquid. Depending upon the speed of rotation, the vortex deepens and finally touches the center of spinning magnet. If a sample bag is present, the vortex drags the bag to the bottom of the container. This results in a confrontation between the delicate membrane of the bag and highly spinning magnet, often resulting in the rupture of sample bag. Sample Saver eliminates this kind of problem. Since the top plate of Sample Saver has no opening in its middle below where the magnet generally spins, vortex never develops. Therefore, the sample bag is protected from the vortex. The liquid, however, rotates, mixes and flows in and out through the openings of Sample Saver. Besides, the openings in the top plate and side wall of Sample saver are small. Sample bag, which is generally large, can not penetrate these openings. This semipermeable action of the Sample Saver, therefore, extends protection to the sample bag from the spin magnet.

SUMMARY, RAMIFICATIONS AND SCOPE

Accordingly, the reader can see that Revolutionary Dialysis Container can be used to dialyze valuable biological samples, safely. It can be carried from one place to another with a proper grip. Used buffer can be drained quickly and completely, and fresh buffer can be added easily without ever touching either the sample bag or the used buffer. Since Sample Saver encloses spin magnet, physical contact between the sample bag and the magnet is eliminated. Through the holes and grooves of Sample Saver, buffer rushes in and out freely during mixing. Lid protects buffer from surface evaporation and air born dust. When not in use the unit with all of its components assembled can be easily stored in a small place.

While the basic details of the invention are shown in FIGS. 1, 2, it is understood that changes in size, shape, structure and materials can be made without greatly departing from the original conception. Some modifications of the invention with advantages and disadvantages are described below.

Base plate contains no handle and no drain tube. The disadvantages are, the unit can not be carried easily, and the buffer can not be drained properly.

Figure 3A:
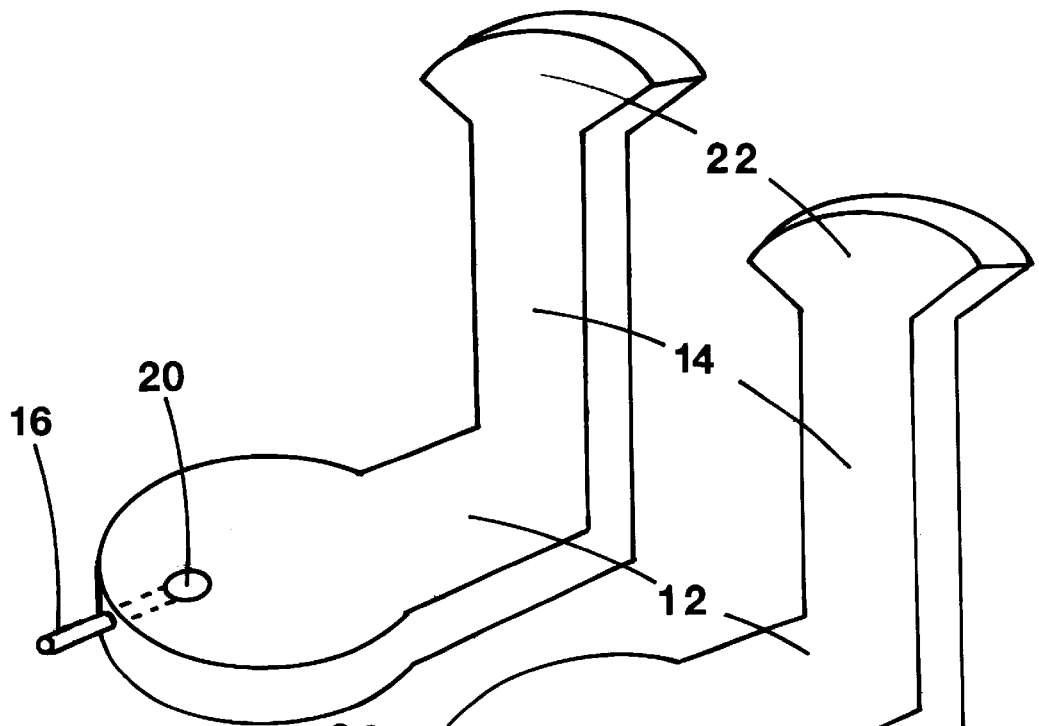
FIG. 3A shows base plate containing one side handle and one drain tube and also the relation between the hole in the top surface and drain tube in the rim.
Figure 3B:
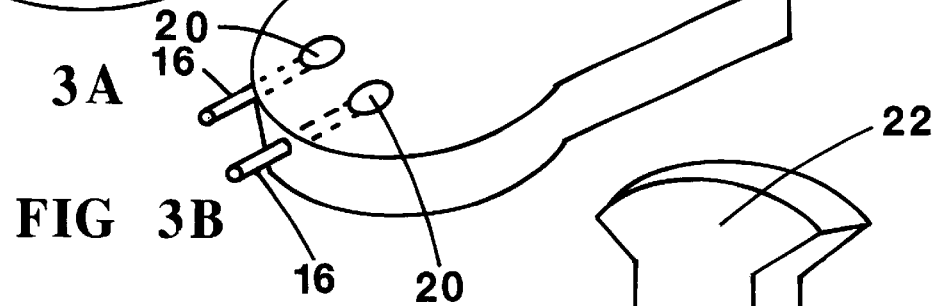
FIG. 3B shows a modified base plate with one side handle and two drain tubes.
Figure 3C:
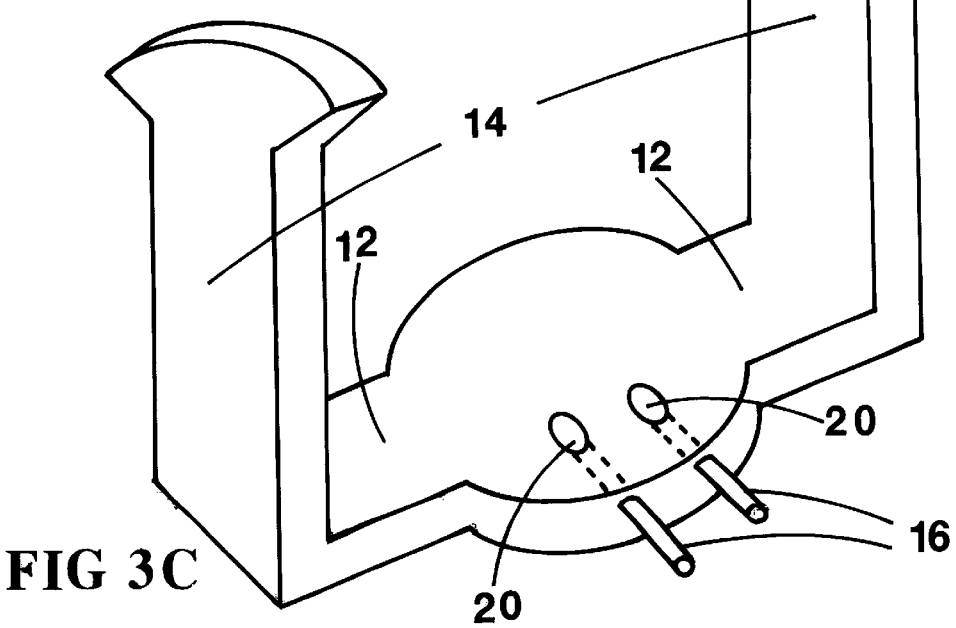
FIG. 3C shows a modified base plate with two drain tubes and with side handles on both sides.

Base plate contains 2 drain tubes in the rim (FIG. 3B). This is useful for draining liquid fast from large containers where the volume of buffer is more.

Also, for automation one tube can be used to pump buffer into reservoir and the other tube can be used to drain used buffer.

Only the top plate of Sample Saver is attached permanently or temporarily suspended across the reservoir between spin magnet and top of the buffer leaving enough fluid to submerge sample bag. If suspended, the disadvantage is that it needs assembly and disassembly for every use.

Figure 4A:
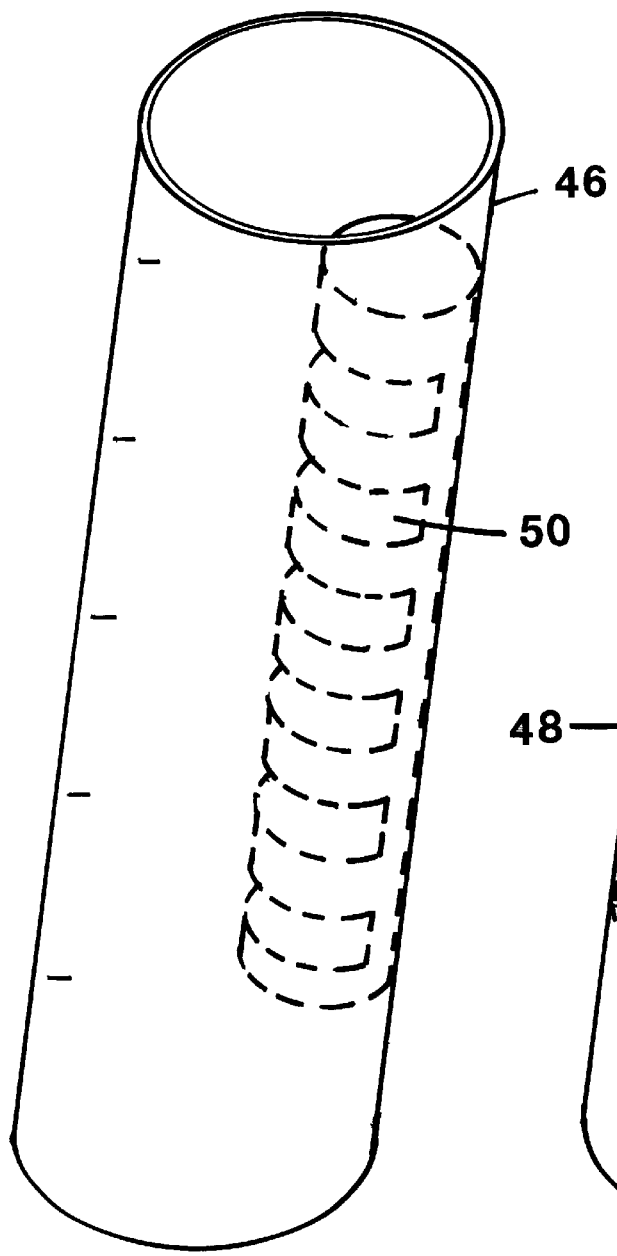
FIG. 4A shows a modified buffer reservoir containing an attached Sample Bag Retainer with transverse slits.
Figure 4B:
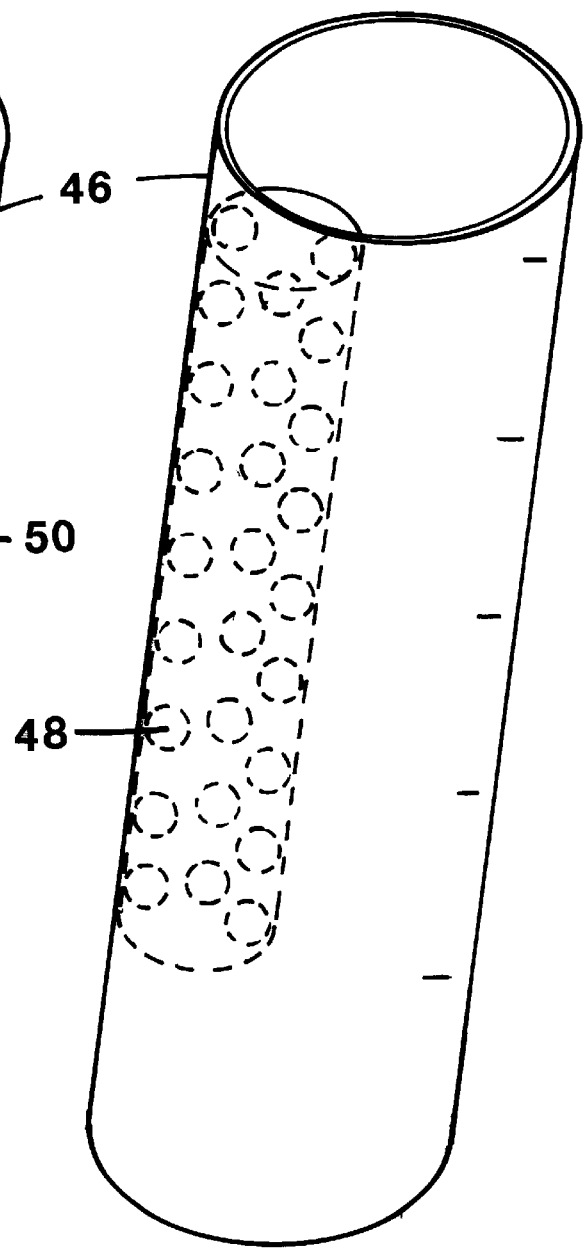
FIG. 4B shows a modified buffer reservoir containing an attached Sample Bag Retainer with holes.

Buffer reservoir contains an additional type of device. This device, Sample Bag Retainer, which is in the form of a tube 46 with transverse slits 50 (FIG. 4A) or holes 48 (FIG. 4B) in its wall, has a closed bottom and an open top. It is attached to the inner surface of buffer reservoir giving some gap at the bottom and at the top. These Sample Bag Retainers can also be hanged freely from the rim of reservoir by a hook. The advantage of Sample Bag Retainer is that dialysis bag can be held inside in a place, safely. However, it has many disadvantages. It accommodates dialysis bags of certain size only. It also decreases the buffer holding capacity of the reservoir. Since it projects out into the chamber, it obstructs other manipulations in the reservoir.

Buffer reservoir contains Sample Bag Retainer in the form of either a sieve or a basket. This type of Sample Bag Retainer is suspended across the buffer chamber, separating spin magnet and dialysis bag, by using side handles. These devices are generally cumbersome to use.

The top plate of Sample Saver contains openings which vary in number, size, shape and pattern of distribution. These features help to accommodate not only increase or decrease in size and shape of the Sample Saver, but also in improving its performance.

Figures 5C, 5D:
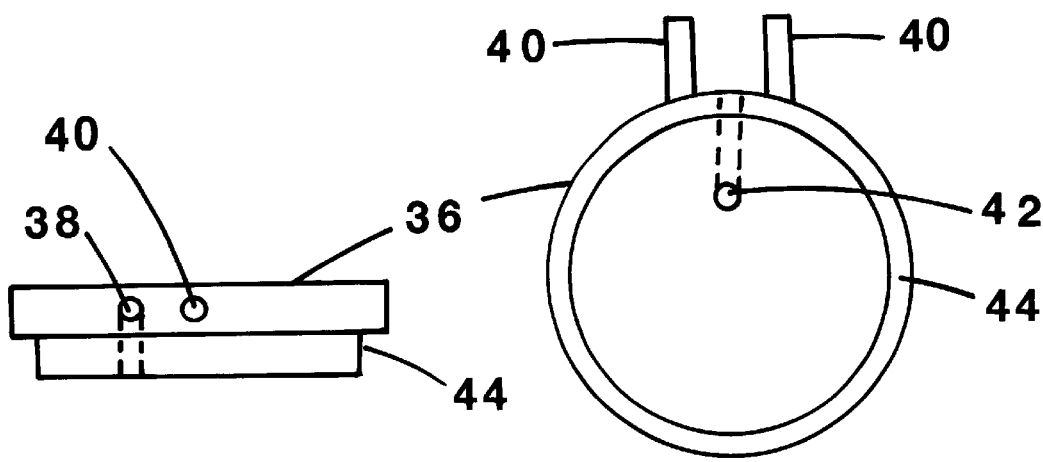
FIG. 5C shows relative positions of groove, hole, and stop pin in the lid.
FIG. 5D shows the lid with two stop pins.

Lid contains two stop pins in the rim (FIG. 5D). Increase in the number of pins corresponding to the number of drain tubes present in the base plate helps in controlling the flow of buffer from reservoir, properly.

Lid is suitably modified and attached to the top end of either reservoir or elongated vertical handle by using a hinge.

From the above described summary, ramifications and scope, it can be seen that one can mix and match several features and fabricate dialysis containers and Sample Savers for different uses. For instance, by eliminating Sample Saver altogether, the rest of the unit can be used as a buffer reservoir for column chromatography. Therefore, the scope of the Revolutionary Dialysis Container should be determined not by the typical embodiment illustrated but by the appended claims and their legal equivalents.

I claim the following:

1. A Dialysis Container for holding a liquid used in dialysis processes, said Dialysis Container comprising: a base plate with a handle extending from said base plate, said handle and said base plate being substantially perpendicular to one another, said handle and said base plate being made from a unitary continuous piece of the same material; a reservoir having lower and upper open ends, said lower open end of the reservoir sitting on said base plate so that said reservoir is substantially parallel to said handle and there is a large enough gap between said reservoir and said handle to provide a grip for a human hand; a lid for opening and closing said upper open end of said reservoir; and a sample saver positioned inside said reservoir and on top of said base plate.

2. The Dialysis Container of claim 1, wherein said base plate, said handle, said reservoir and said lid are all made of acrylic.

3. The Dialysis Container of claim 1, wherein said handle has upper and lower ends, said handle being wider at said upper end of said handle then it is at said lower end of said handle for creating a non-slippery grip.

4. The Dialysis Container of claim 1, wherein said base plate has a rim and a tube in said rim for draining the liquid from said reservoir.

5. The Dialysis Container of claim 4, wherein said base plate has a top and a bottom and a hole in said top of said base plate, said hole being encircled by said reservoir and in liquid communication with said drain tube.

6. The Dialysis Container of claim 5, wherein said lid has a rim with a pin in said rim for attaching said drain tube to said pin and stopping the flow of the liquid from said reservoir.

7. The Dialysis Container of claim 6, wherein said lid has a hole which opens into said reservoir to provide ventilation.

8. The Dialysis Container of claim 1, wherein said reservoir has an outer surface with graduation marks on said outer surface for indicating the volume of the liquid in said reservoir.

9. The Dialysis Container of claim 8, wherein said reservoir is tubular in shape.

10. The Dialysis Container of claim 9, wherein said reservoir is transparent.

11. A Dialysis Container for holding a liquid used in dialysis processes, said Dialysis Container, comprising: a base plate with a handle extending from said base plate; a reservoir having lower and upper open ends, said lower open end of said reservoir sitting on said base plate; a lid for opening and closing said upper open end of said reservoir; and a sample saver positioned inside said reservoir on top of said base plate; said sample saver comprising a horizontal flat top plate attached to a vertical side wall, said horizontal flat top plate comprising a plurality of holes situated away from the center of said horizontal flat top plate and/or said vertical side wall having a plurality of openings cut through said vertical side wall.

12. The Dialysis Container of claim 1, wherein said base plate, said handle, said reservoir and said lid are all made of acrylic.

13. The Dialysis Container of claim 1, wherein said handle has upper and lower ends, said handle being wider at said upper end of said handle then it is at said lower end of said handle for creating a non-slippery grip.

14. The Dialysis Container of claim 1, wherein said base plate has a rim and a tube in said rim for draining the liquid from said reservoir.

15. The Dialysis Container of claim 4, wherein said base plate has a top and a bottom and a hole in said top of said base plate, said hole being encircled by said reservoir and in liquid communication with said drain tube.

16. The Dialysis Container of claim 5, wherein said lid has a rim with a pin in said rim for attaching said drain tube to said pin and stopping the flow of the liquid from said reservoir.

17. The Dialysis Container of claim 16, wherein said lid has a hole which opens into said reservoir to provide ventilation.

18. The Dialysis Container of claim 11, wherein said reservoir has an outer surface with graduation marks on said outer surface for indicating the volume of the liquid in said reservoir.

19. The Dialysis Container of claim 18, wherein said reservoir is tubular in shape.

20. The Dialysis Container of claim 19, wherein said reservoir is transparent.

21. The Dialysis Container of claim 11, wherein said horizontal side plate and said vertical side wall enclose a movable member for stirring the liquid.

22. The Dialysis Container of claim 11, wherein said movable member is a magnet.

* * * * *